ROSE PLANT
Filed Oct. 6, 1964
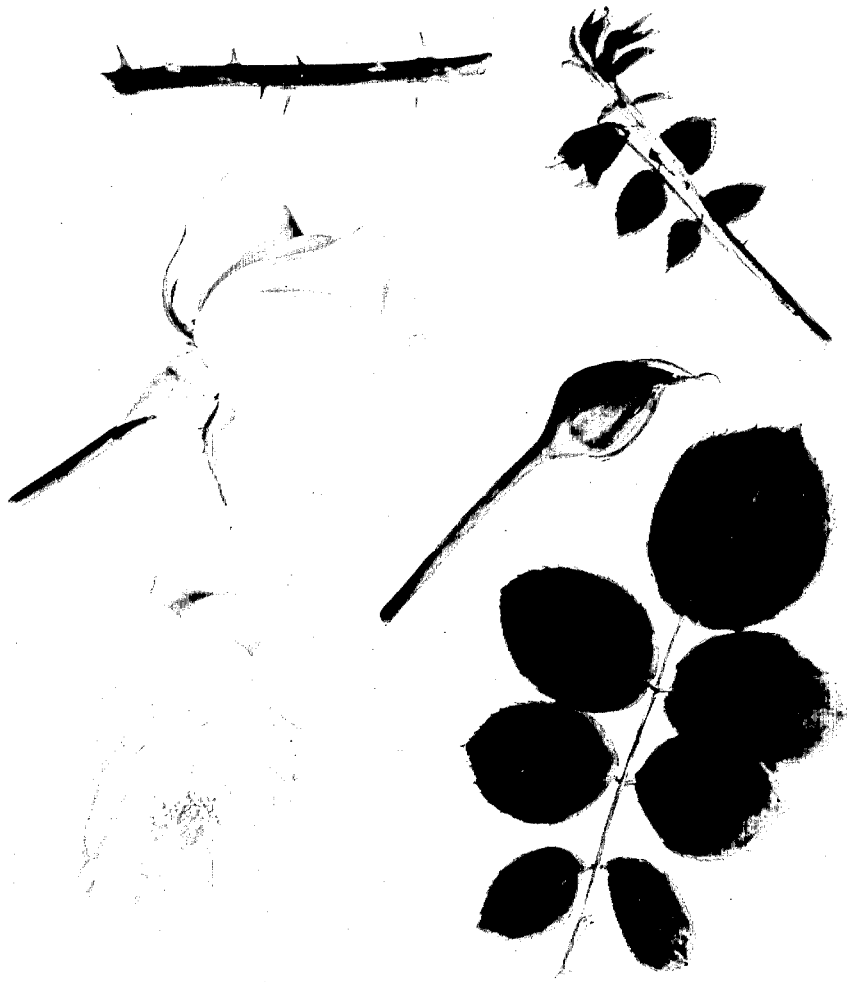
Inventor.
Herbert Robinson
By: Robb & Robb
Attorneys.

United States Patent Office

Plant Pat. 2,582
Patented Dec. 28, 1965

2,582
ROSE PLANT

Herbert Robinson, Burbage, Hinckley, England, assignor to Jackson & Perkins Company, Newark, N.Y., a corporation of New York Filed Oct. 6, 1964, Ser. No. 402,043
1 Claim. (Cl. Plt.—18)

The present invention relates to a new and distinct variety of rose plant of the hybrid tea class, which was originated by me by crossing an unnamed and unpatented seedling of "Peace" (U.S. Plant Patent No. 591) × "Gail Borden" (U.S. Plant Patent No. 1618) with an unnamed and unpatented seedling of the rose variety known as "Dorothy Peach" (unpatented).

The primary objective of this breeding was to produce a new and improved Hybrid Tea rose variety having greater blooming ability than the variety "Peace," and which bears more colorful Pink flowers than the variety "Peace." This objective was fully achieved, along with other desirable improvements, as evidenced by the following unique combination of characteristics which are outstanding in the new variety and which distinguish it from its parents as well as from all other varieties of which I am aware:

(1) An upright habit of plant growth;
(2) A free blooming habit, with consequent greater abundance of flowers than the variety "Peace";
(3) A flower form similar to that of the variety "Peace"; and
(4) A distinctive and attractive general color tonality of the flowers corresponding to Deep Rose Pink, lightly overcast with Rose Pink.

Asexual reproduction of the new variety by budding, as performed at Newark, New York, U.S.A., and also at Pleasanton, California, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in color illustration of this character.

The following is a detailed description of my new variety, with color terminology in accordance with Ridgway's Color Standards and Nomenclature:

Parentage: Seedling.
*Seed parent.*—An unnamed seedling of "Peace" × "Gail Borden."
*Pollen parent.*—An unnamed seedling of the rose "Dorothy Peach."
Classification:
*Botanic.*—Hybrid Tea.
*Commercial.*—Hybrid Tea.

*Flower*

(Observations made from specimens grown in greenhouse at Newark, New York, U.S.A., in the early afternoon during the latter part of the month of may.)

Blooming Habit: Recurrent—continuous.
Bud:
*Size.*—Large.
*Form.*—Ovoid; is not affected by wet or hot weather.
*Color.*—When sepals first divide—Light Coral Red, Plate 13. When petals begin to unfurl—Rose Color, Plate 12, lightly overcast with Deep Rose Pink, Plate 12. When half-blown—inside of petals: Thulite Pink, Plate 26, lightly overcast with Spinel Pink, Plate 26 in the lower half of the petal and the outer edge of the petal. Reverse of petals: Spinel Pink, Plate 26, overcast with Thulite Pink, Plate 26, in the center of the petal.
*Sepals.*—Smooth edge; stand up when petals begin to unfurl. Color—inside: Malachite Green, Plate 32; outside: Cedar Green, Plate 6.
*Calyx.*—Color—Cedar Green, Plate 6. Shape—pear. Size—broad. Aspect—smooth. Odor when rubbed—none.
*Peduncle.* — Length — medium. Aspect — rough. Strength—erect; slender. Color—Forest Green, Plate 17.
*Opening.*—Opens up well; is not affected by adverse weather conditions.

Bloom:
*Size.*—Large. Average size when fully expanded—6 inches.
*Borne.*—Both singly and several together; free blooming, with many blooms per plant.
*Stems.*—Medium length; strong.
*Form (when first open).*—High centered. Permanence—retains its form to the end, but outer petals curl back. Petalage—double (full but open center). Number of petals under normal conditions—from 25 to 30.
*Color.*—Center of flower—Deep Rose Pink, Plate 12, very lightly overcast with Rose Color, Plate 12. Outer petals—Thulite Pink, Plate 26, very lightly overcast with Deep Rose Pink, Plate 12. Base of petals (aiglet)—Empire Yellow, Plate 4. Inside of petals—Deep Rose Pink, Plate 12, lightly overcast with Rose Pink, Plate 12. Reverse of petals—Rose Pink, Plate 12, lightly overcast with Deep Rose Pink, Plate 12, with lower half of petal faintly overcast with Light Orange-Yellow, Plate 3. General tonality from a distance—Deep Rose Pink, Plate 12, lightly overcast with Rose Pink, Plate 12.
*Discoloration.*—General tonality at end of first day—Deep Rose Pink, Plate 12, lightly overcast with Rose Pink, Plate 12. Second day—Deep Rose Pink, Plate 12, overcast with Rose Pink, Plate 12. Third day—Deep Rose Pink, Plate 12, overcast with Rose Pink, Plate 12.

Petals:
*Texture.*—Leathery; is not affected by wet or hot weather
*Appearance.*—Inside—satiny. Outside—shiny.
*Form.*—Oval; notched slightly.
*Arrangement.*—Imbricated (regularly arranged shingle-like).
*Petaloids in center.*—Few; large.
*Persistence.*—Drop off cleanly.
*Fragrance.*—Moderate. Nature—tea (average hybrid tea scent).
*Lasting quality.*—On the plant—long. As cut flower—long.

*Genital organs*

Stamens: Anthers—large; many; regularly arranged around styles.
*Color.*—Cadmium Yellow, Plate 3.
Stamens, Filaments (threads): Medium length.
*Color.*—Geranium Pink, Plate 1.
Pollen:
*Color.*—Pale Yellow-Orange, Plate 3.
Styles: Bunched; uneven length; short; thin.
Stigmas:
*Color.*—Antimony Yellow, Plate 15.
Ovaries: All enclosed in calyx.
Hips: None.
Seeds: None.

*Plant*

Form: Bush.
Growth: Vigorous; upright and bushy.
Foliage: Compound of from 5 to 7 leaflets.
*Size.*—Large.
*Quantity.*—Abundant.
*Color.*—New foliage—upper side:—Yellowish Olive, Plate 30, overcast with Bordeaux, Plate 12; under side:—Garnet Brown, Plate 1, with center of leaf Rainette Green, Plate 31. Old foliage—upper side: Cress Green, Plate 31; under side—Spinach Green, Plate 5.
*Shape.*—Oval pointed.
*Texture.*—Upper side—glossy. Under side—smooth.
*Ribs and veins.*—Ordinary.
*Edge.*—Serrated (saw-toothed).
*Serration.*—Both double and single; small.
*Leaf stem.*—Color—Light Cress Green, Plate 31. Under side—prickly.
*Stipules.*—Medium length; smooth.
Wood:
*New wood.*—Color—Yellowish Oil Green, Plate 5. Bark—smooth.
*Old wood.*—Color—Cress Green, Plate 31. Bark—smooth.

Thorns:
*Thorns.*—Quantity—on main stalks from base: ordinary; on laterals from stalk: ordinary. Form—narrow base; medium length; some straight and some hooked downward. Color (when young)—Acajou Red, Plate 13. Position—irregular.
*Prickles.*—Quantity—on main stalks from base: none. On laterals: none.
*Short needles.*—Quantity—on main stalks: none. On laterals: none.

I claim:

A new and distinct variety of rose plant of the hybrid tea class, substantially as herein shown and described, characterized particularly as to novelty by the unique combination of an upright habit of plant growth, a free blooming habit, with consequent greater abundance of flowers than the variety "Peace," a flower form similar to that of the variety "Peace," and a distincitive and attractive general color tonality of the flowers corresponding to Deep Rose Pink, lightly overcast with Rose Pink.

No references cited.

ABRAHAM G. STONE, *Primary Examiner.*